(12) United States Patent
Gregory et al.

(10) Patent No.: US 9,435,790 B2
(45) Date of Patent: Sep. 6, 2016

(54) CELL SEPARATION TECHNIQUE

(75) Inventors: Christopher Gregory, Edinburgh (GB); John Pound, Edinburgh (GB)

(73) Assignee: Grampian Biopartners Limited, Aberdeen (GB)

( * ) Notice: Subject to any disclaimer, the term of this patent is extended or adjusted under 35 U.S.C. 154(b) by 1160 days.

(21) Appl. No.: 13/142,046

(22) PCT Filed: Dec. 23, 2009

(86) PCT No.: PCT/GB2009/002948
§ 371 (c)(1),
(2), (4) Date: Jun. 24, 2011

(87) PCT Pub. No.: WO2010/073014
PCT Pub. Date: Jul. 1, 2010

(65) Prior Publication Data
US 2011/0256581 A1    Oct. 20, 2011

(30) Foreign Application Priority Data
Dec. 24, 2008 (GB) .................... 0823553.3

(51) Int. Cl.
*G01N 33/50* (2006.01)

(52) U.S. Cl.
CPC ....... *G01N 33/5032* (2013.01); *G01N 2400/22* (2013.01)

(58) Field of Classification Search
None
See application file for complete search history.

(56) References Cited

U.S. PATENT DOCUMENTS

| 4,452,773 A | 6/1984 | Molday |
| 5,411,863 A | 5/1995 | Miltenyi |
| 6,664,047 B1 * | 12/2003 | Haugland et al. ........... 435/6.12 |
| 2001/0051372 A1 | 12/2001 | Yin et al. |
| 2004/0249438 A1 | 12/2004 | Lefranc et al. |
| 2008/0044811 A1 | 2/2008 | Haugland et al. |

FOREIGN PATENT DOCUMENTS

| WO | WO 99/58977 | 11/1999 |
| WO | WO 2009/071892 | 7/2009 |

OTHER PUBLICATIONS

Park et al. "Comparison of labeling efficiency of different magnetic nanoparticles into stem cells" (2008—available online Jun. 7, 2007) Colloids and Surfaces A: Physiochemical Engineering Aspects, vol. 313-314: 145-149.*
Minamimura, T. et al., "Tumor regression by inductive hyperthermia combined with hepatic embolization using dextran magnetite-incorporated microspheres in rats", International Journal of Oncology, Demetrios A. Spandido Ed. & Pub, GR, Jun. 1, 2000, vol. 16, No. 6, pp. 1153-1158.
Miltenyi, S., et al., (1990) "High Gradient Magnetic Cell Seperation with MACS", Cytometry, 11, 231-238.
Anonymous, Miltenyi Biotech GmbH: "CD43 (Ly-48) Microbeads" Miltenyi Datasheet 130-049-801, 2006.
Anonymous, Miltenyi Biotech GmbH: The CiniMACS System, Touch Briefings, 2007.
Anonymous, Miltenyi Biotech GmbH: "Basic Microbeads", Miltenyi Datasheet 130-048-001, 2005.
3rd Party Observations from Prosecution of EP2367930. Submitted on Jun. 17, 2013.
Sommer, I. Developmental Biology, vol. 83 (2), 1981, p. 311-327. ISSN: 0012-1606.

* cited by examiner

*Primary Examiner* — Robert Yamasaki
*Assistant Examiner* — Teresa E Knight
(74) *Attorney, Agent, or Firm* — John W. Boger

(57) ABSTRACT

In a first aspect, the present invention provides a method of removing non-viable cells from a cell population, said method comprising contacting a cell population with a compound under conditions suitable to permit binding between the compound and any non-viable cells present in the cell culture and removing at least some of the compound from said cell population. The invention further provides compositions suitable for use in these methods, further uses of such compositions and various other systems and kits.

4 Claims, 11 Drawing Sheets

CELL SEPARATION TECHNIQUE

CROSS REFERENCE TO RELATED APPLICATIONS

Figure 1:
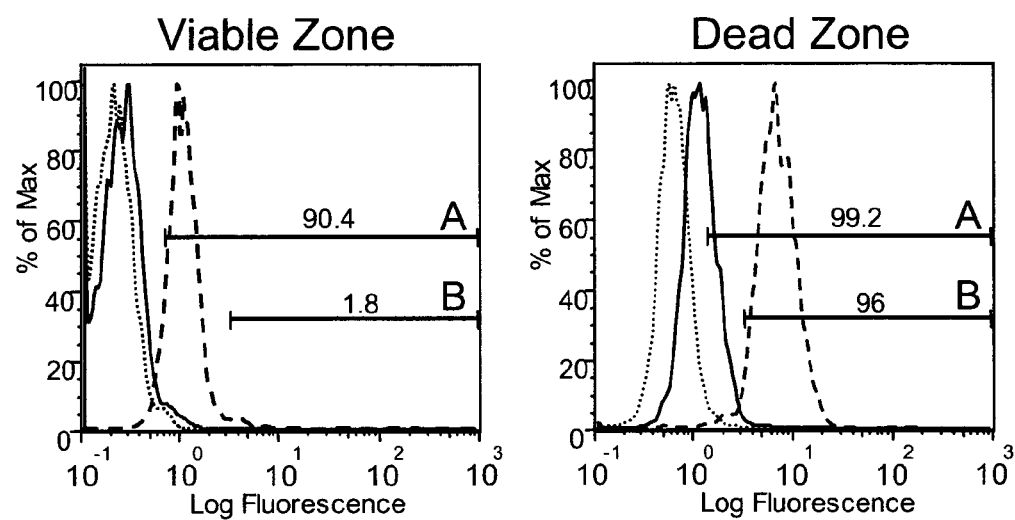

This application is a United States Application under 35 USC §371 claiming benefit of PCT/GB2009/002948, filed Dec. 23, 2009, which claims priority to GB 0823553.3, filed Dec. 24, 2008, the contents of each of which are incorporated herein by reference.

FIELD OF THE INVENTION

The present invention relates to methods for removing non-viable cells from cell populations such as cell cultures, compositions suitable for use in these methods, further uses of such compositions and various other systems and kits.

BACKGROUND OF THE INVENTION

Cells die for many reasons, including normal physiological processes that control cell numbers in all tissues. Cell death can occur via natural physiological processes (the best known being apoptosis) as well as through accidental damage (necrosis)—caused in cells in culture, for example, by shear stress in culture vessels. In our bodies, dead cells are efficiently removed by phagocytic cells such as macrophages, otherwise they can cause tissue damage and can contribute to the development of disease. If they remain uncleared (as generally occurs in cell cultures), apoptotic cells progress to become necrotic (sometimes referred to as 'secondary necrosis'). This progression is characterised by loss of plasma membrane integrity.

Current assays of cell viability are many and varied, simple and complex. For example, the simplest assays, such as vital dye exclusion, assess the ability of dyes that are excluded from viable cells to enter dead cells. Commonly-used examples of such dyes are trypan blue, propidium iodide and ethidium bromide. More complex assays include release of macromolecules, such as the enzyme lactate dehydrogenase (LDH), whose activity can be assessed via its activity on a suitable chromogenic substrate. These assays, however, are restricted to detection of the necrotic stage of cell death since both require loss of plasma membrane integrity for positivity. Full appreciation of the true viability of a population at a given time requires assessment of both dying (apoptotic) and dead (necrotic) cells. Full appreciation of the true viability of a population at a given time requires assessment of both dying (apoptotic) and dead (necrotic) cells. Assays of dying, apoptotic, cells are generally complex, requiring multiple steps (for example TUNEL-type assays and assays of caspase activation) and this can lead to technical problems such as false-positives. A common method makes use of the early changes in plasma membrane phospholipid asymmetry that are a hallmark of apoptosis. The phospholipid-binding protein, annexin V, under relatively high concentrations of extracellular $Ca^{2+}$, binds to the phospholipid, phosphatidylserine (PS), that is rapidly exposed on the surface of apoptotic cells prior to loss of plasma membrane integrity. Antibody-mediated detection of PS, such as via Immunosolv's imab6 monoclonal antibody, obviate the need for extracellular $Ca^{2+}$. There are currently a limited range of methods and kits available for achieving the selective removal of dying/dead cells from cell cultures. These include, for example, Miltenyi kits and imab6-coupled Dead-Cert™Nanoparticles produced by Immunosolv.

Despite the availability of these reagents and kits, there is a need for new improved techniques as although dyes like trypan blue can be used to accurately detect or label dead cells, it is not capable of highlighting dying cells. Furthermore, annexin V is $Ca^{2+}$-dependent and thus inconvenient for measurement under conditions of low $Ca^{2+}$ as might occur in suspension cultures commonly used in biomanufacturing.

In addition to the above, there is a need for additional methods of manipulating non-viable cells, improving the viability of cell cultures and the storage and transport of cells. Improved protocols for cell line establishment and productivity are also needed. Any method which lowers background activity due to dead cells and improves transfection efficiency would also represent a significant improvement over the prior art.

There is also a need for methods which manipulate cells at late stages of apoptosis as early apoptotic cells, which produce growth factors such as lactoferrin, can have positive effects on their surroundings [Bournazou, 2008 #3517].

SUMMARY OF THE INVENTION

The present invention is based on the finding that, as cells die, the numbers of certain cell components increase (or that their accessibility to certain exogenous compounds increases). In addition, the inventors have discovered that these cell components are capable of binding certain compounds, particularly, for example, non-protein compounds. As such, since dying and/or dead cells possess more of these binding sites than viable cells, the present invention provides methods and compositions suitable for use in separating dying, and/or necrotic/dead cells from viable cells.

In a first aspect, the present invention provides a method of removing non-viable cells from a cell population, said method comprising the steps of contacting a cell population with a compound under conditions suitable to permit binding between the compound and any non-viable cells present in the cell culture and removing at least some of the compound from said cell population, wherein the compound is not a proteinacious compound.

The term "proteinacious" compound is intended to encompass proteins, peptides, amino acids and/or antibodies/antibody fragments. As such, it should be understood that the compound provided by the first aspect of this invention is not a protein, peptide, amino acid or antibody/antibody fragment.

One of skill in this field will appreciate that a cell population may comprise viable, dying, and/or necrotic (dead) cells and it is to be understood that cells which are dying, necrotic or dead are hereinafter collectively termed "non-viable cells".

In addition, the term "cell population" may include cell cultures comprising, for example, eukaryotic cells such as mammalian, particularly human, cells. In this regard, the present invention may provide methods and compositions suitable for use with populations of these cells types and/or in the culture of specialised cell types such as, for example, stem cells (adult and/or embryonic stem cells), cardiac cells, epithelial cells, endothelial cells, skin (dermal) cells, nerve cells, muscle cells, cells of the circulatory (i.e. blood) system and/or other cell types such as, for example, lymphocytes, osteocytes and/or chondrocytes. Examples are shown in Table 1.

TABLE 1

Examples of cell types for which removal of non-viable cells has been successfully demonstrated using the present invention

| Cell | Species | Line or Primary |
|---|---|---|
| NSO myeloma | Mouse | Line |
| Hybridomas | Mouse | Lines |
| Burkitt lymphomas | Human | Lines |
| Lambda-MYC lymphomas | Mouse | Lines |
| Lambda-MYC lymphomas | Mouse | Primary |
| Neutrophil | Human | Primary |
| Thymocyte | Mouse | Primary |
| Macrophage | Mouse | Primary |
| THP-1 monocyte/macrophage | Human | Line |
| RAW-264 monocyte/macrophage | Mouse | Line |
| J774 monocyte/macrophage | Mouse | Line |
| Bladder carcinoma | Human | Primary |
| Foetal liver | Mouse | Primary |
| A549 lung carcinoma | Human | Line |
| Embryonic stem cell lines | Mouse | Lines |
| Embryonic stem cell lines | Human | Lines |
| Burkitt lymphoma xenograft | Human in Mouse | Primary |
| CHO | Hamster | Lines |
| U937 monocytic leukaemia | Human | Line |
| L929 fibroblasts | Mouse | Line |
| Dendritic cells | Mouse | Primary |
| HL60 leukaemia | Human | Line |
| Monomac 6 leukaemia | Human | Line |
| H345 lung carcinoma | Human | Line |

In addition, the compositions and methods of this invention may be used to remove dead cells from cell cultures comprising hybridoma cells for the production of monoclonal antibodies.

In addition, the term "cell population" may include populations of primary cells for example as derived from bone marrow (for transplantation), cells for use in in vitro fertilisation techniques (such as oocytes, sperm and fertilised oocytes etc.). Cell populations may also include, for example blood samples or donations which comprise either whole blood or fractions thereof (for example white blood cells). As such, a "cell population" may include blood derived from the umbilical cord.

It will be readily understood that there are many different ways in which cells can be cultured and the precise culture conditions and/or nutritional requirements will vary depending upon the exact cell type being cultured. Nevertheless, irrespective of the cell type or precise conditions under which the cells are being cultured, it is desirable to remove non-viable cells from cell cultures so as to maintain high levels of viable cells and/or improve the cell culture productivity.

The proportion of viable and non-viable cells present in a cell population such as a cell culture may vary depending on, for example, the age of the cell culture, the conditions in which the population is maintained and/or the availability of nutrients. Generally speaking, the older a population of cells, and the lower the availability of one or more of the nutrients required for cell growth, the more non-viable cells may be present. The total number of non-viable cells present in a cell population can negatively impact upon the total number of viable cells present and thus it is desirable to remove non-viable cells from cell populations such as, for example cell cultures. Cell death may occur in cell populations for a variety of additional reasons, for example as a result of the use of drugs that kill cells that are lacking drug-selection markers—as used in the selection of stable transfectants, for example—or as a result of physical stress, such as shear stress in certain bioreactors or as a consequence of handling procedures or as a result of freeze/thaw trauma.

In view of the above, it should be understood that removing the compound contacted with a cell population such as a cell culture, under conditions suitable to permit binding with any non-viable cells present in the cell culture, has the effect of removing non-viable cells from the cell culture.

The methods provided by this invention may be used continually, to ensure the number of non-viable cells present in a cell population is kept to a minimum. Alternatively, the methods described herein may be used periodically or occasionally.

A further effect of removing non-viable cells from cell populations is that it may increase the proportion of viable cells present in a cell culture and/or to improve cell culture productivity.

It should be understood that the term "viable" cell encompasses any cell that is not dead or that is not irreversibly committed to death. Viable cells are capable of living cell functions under physiological conditions, for example transcription and translation of proteins and of metabolic homeostasis. Non-viable cells encompass cells that are dead or that are irreversibly committed to die, such as cells undergoing programmed cell death.

The phrase "improved cell culture productivity" or "improved viability", relates to any increase in the proportion of viable cells present in a particular cell population. By way of example, a typical cell culture may comprise a population of viable cells not exceeding about 30% or less of the total number of cells—viable, dead, and dying, present in the cell culture. By using the compounds and methods described herein, it may be possible to remove at least a portion of the non-viable cells present in the cell culture, such that the proportion of viable cells is increased. It is to be expected that by using the compounds and/or methods of this invention to remove non-viable cells from a cell culture, the proportion of viable cells present may increase from about, for example, 30% of the total cell population, to about, for example, 40%, 50%, 60%, 70%, 80%, 90%, 95% and in some embodiments approximately 99% of the total cell population. In other embodiment, the proportion of viable cells present in a cell culture may be increased to about 100%.

Insofar as the compounds provided by this invention are capable of selectively and/or preferentially binding to non-viable cells, they may be particularly useful in the field of cell culture and/or in methods or processes which require high levels of cell productivity in order to generate sufficient yields of cells or particular products expressed by said cells. In addition, the methods described herein may be used to improve the quality of products produced by cells such as, for example, nucleic acid, proteins and the like. In one embodiment, the compounds and methods provided by this invention may find particular use in processes for the generation of monoclonal antibodies and/or recombinant proteins, which processes routinely involve culturing large numbers of cells. In these processes, the number or proportion of viable cells in a cell culture is positively correlated with product yield. Non-viable cells, which negatively affect cell viability and/or cell culture productivity, can also negatively impact upon product yield.

In one embodiment, the compound is a compound capable of binding cell components present on or in non-viable cells. In other embodiments, the compound is not a protein. As stated, these cells components increase in number and/or accessibility as cells die and as such, dead cells possess more of these binding sites than viable cells. Thus, in a further embodiment, the compound may be a compound capable of binding cell components which increase in number and/or accessibility as a cell dies. The term "compounds" may include, for example, natural or synthetic polymers, particularly non-protein polymers such as, for example polysaccharides.

Suitable polysaccharides may include, for example, complex branched glucan molecules. One of skill in this field will readily understand that such molecules may exist in a variety of forms and it should be understood that polysaccharides of many different sizes and forms may be encompassed within the scope of this invention.

By way of example, the compound, for example polysaccharide, described herein may be about 10 to about 150 kDa in size, although since the precise structure of the compounds suitable for use in this invention may be highly variable, compounds which have molecular masses smaller or greater than the abovementioned range, may also be useful. Indeed, provided the compound is capable of binding to cell components which increase in number/accessibility as cells die, it may find application in the present invention.

In one embodiment, the compound is the polysaccharide dextran. Dextran comprises a chain of α-1,6 glycosidic linked glucose molecules and dextran compounds suitable for use in the methods and compositions described herein may comprise two or more α-1,6 glycosidic linked glucose molecules. In addition, dextran may further comprise branching moieties which extend from the α-1,6 glycosidic linked glucose chain via α-1,4, α-1,2 and/or α-1,3 linkages.

As such, dextran compounds suitable for use in this invention, may comprise 2 or more α-1,6 glycosidic linked glucose molecules as well as one or more α-1,4, α-1,2 and/or α-1,3 linked branching moieties.

The polysaccharide dextran has a number of applications in cell biology, including sedimentation of red blood cells (aggregation under conditions of low shear stress), assessment of permeability (see for example [Wakamoto, 2008 #3520; [Graziadei, 1991 #3514], tracking of phagocytes [Pawelczyk, 2008 #3521], neural pathway tracing [Reiner, 2000 #3523] and as an endocytosis marker [Allavena, 1998 #2948]. In macrophages, dextran enters endocytic vesicles mainly after binding mannose receptors [Allavena, 1998 #2948]. Dextran is also used clinically as a blood volume expander for the treatment of shock or impending shock when blood or blood products are not available. Dextran also has application in the prophylaxis of thrombosis.

In addition, modified dextran compounds (otherwise known as "dextran analogues") may also be used. By way of example, carboxylated and/or amino—dextran compounds may be particularly useful.

Non protein compounds such as, for example, polysaccharides, (including dextran), are particularly useful where cells, cell cultures and/or products derived therefrom (for example nucleic acids, proteins and/or recombinant proteins) are to have clinical or therapeutic applications. In particular, the methods, compositions and uses described herein may be protein free and thus avoid the use of xeno-proteins such as antibodies (monoclonal, humanised or the like).

In addition, dextran is soluble and as such can be easily formulated as an aqueous solution for addition to, for example, cell cultures. Dextran is also particularly stable and can be stored for prolonged periods of time prior to use.

In addition to the above, polysaccharides such as dextran have the further advantage of being able to be used at a variety of temperatures and under divalent cation-free conditions which prevent cell clumping and improve cell separation.

Cell populations may be contacted with the compounds described herein in a number of ways. In one embodiment, the compound may be added directly to a cell population under conditions suitable to allow binding between any non-viable cells present in the cell culture and the compound. In other embodiments, the compound may be prepared or formulated as an aqueous solution which can be added to a cell population.

In a further embodiment, the compound may be packed into a column to which a cell population may be added. In this way, under the action of gravity and/or with the aid of a pump, a cell population may be allowed to pass through and over the compound such that any non-viable cells present in the cell population bind thereto.

In a further embodiment, the compound may be adhered, bound, immobilised and/or otherwise associated with a scaffold material which can be deposited and/or submerged in a cell suspension or cell culture. Advantageously, scaffold materials of particular use may be permeable or porous such that cells can pass through and over the material. By placing a scaffold material comprising an immobilised compound of this invention, into a cell population and incubating the scaffold with the population under conditions suitable to permit binding between any non-viable cells present in the cell population and the compound of the scaffold, when the scaffold is removed, so too are any non-viable cells bound thereto.

In one embodiment of this invention, the compound is provided in the form a particle, for example a micro- or nanoparticle. In certain embodiments the micro- or nanoparticles suitable for use in this invention may take the form of small beads or microspheres of between 10-500 nm in diameter. In other embodiments, the micro- or nanoparticles may be about 50-450 nm, about 100-400 nm, about 150-350 nm or about 200-300 nm. In one embodiment, the micro- or nanoparticles may be about 250 nm in diameter.

As stated, the micro- or nanoparticles may comprise or consist of any of the compounds described herein. For example, the micro- or nanoparticles may comprise or consist of polysaccharides such as, for example, dextran.

In one embodiment, the micro- or nanoparticle may comprise a core material coated with a compound provided by this invention.

In a further embodiment, the micro- or nanoparticles may further comprise a magnetic material. In certain embodiments, the magnetic material may form the core region of the micro- or nanoparticle or a component of a coating applied to a core material. In other embodiments, the micro- or nanaoparticles may comprise a magnetic core coated with a compound according to this invention.

Such particles may be known as magnetic, paramagnetic or superparamagnetic particles. Advantageously, superparamagnetic particles suitable for use in this invention may comprise a magnetite core coated with (or surrounded by a shell of) a polysaccharide such as, for example, dextran.

Dextran-coated superparamagnetic nanoparticles are used currently in MRI applications and therefore low contamination of therapeutics with these particles would be low risk for regulators. For example, Resovist® is an organ-specific MRI contrast agent, used for the detection and characterization of especially small focal liver lesions. They have also been described as suitable for use in killing tumour cells via the heat that can be induced following their uptake by metabolically highly active tumour cells (magnetic fluid hyperthermia) (see [Minamimura, 2000 #3518; Ito, 2003 #3519].

The compound may be tagged or labelled in some way. For example, the compound, whether in the form of a micro- or nanoparticle or not, may comprise a protein tag and/or fluorescent marker. In certain embodiments the protein tag may take the form of an antibody or a protein or short peptide such as, for example, a histidine tag or GST tag. Suitable fluorescent molecules are known in the art include, for example, fluorophores, such as FITC, rhodamine or Texas Red. Other types of molecule which may be used include green fluorescent protein (GFP), radiolabelled moieties and the like.

In addition to the above, methods of removing at least a proportion of the compound from a cell population such as a cell culture may vary depending on the precise nature and form of the compound and may include, for example filtration, density separation, flow cytometry/cell sorting and/or affinity chromatography techniques. Accordingly, any form of compound or particle which is capable of being selectively removed from, for example, a cell culture, may be suitable for use and such forms of compound and/or particle (including the micro- or nanoparticles and magnetic particles discussed above) shall be referred to hereinafter as "recoverable particles".

Where the recoverable particles take the form of magnetic or superparamagnetic particles, they may easily be recovered or removed from a cell population such as a cell culture via the application of a magnetic field (by means of a magnet, electromagnet or the like). Briefly, by immobilizing or collecting the particles using a magnetic field, it is possible to, for example, pipette or decant the culture from the collected magnetic particles. In this way cultures removed by pipetting or decanting comprise substantially viable cells, the non-viable being retained bound to the compound of the magnetic particles held by the magnetic field.

Where the compound is provided in the form of a column to which a cell population may be added, the eluate collected from the column (i.e. the material which passes through the column) may substantially comprise viable cells, the non-viable having been retained in the column bound to the compound.

Where the compound is provided in the form of a tagged or labeled compound, techniques such as flow cytometry or affinity chromatography may be used to remove the compound from the cell population. For example, where the compound is modified to include a histidine or GST tag, the appropriate affinity matrix (such as nickel/cobalt ion columns and/or glutathione Sepharose) may be used to separate the compound from the cells. Where the protein tag or label is an antibody, any affinity matrix comprising the relevant immobilized antigen may be used.

In embodiments where the compound comprises a fluorescent tag, flow cytometry or cell sorting techniques, which separate elements based on the presence of particular fluorescent tags may be used.

Other means of separating recoverable particles for, for example, cell cultures include the use of centrifugation techniques. Such techniques may be used to pellet recoverable particles from solution to leave a supernatant comprising, for example, substantially viable cells—the non-viable cells being bound to the pelleted particles.

The present inventors have ascertained that while the compounds described herein bind selectively or preferentially to non-viable cells, viable cells also exhibit some expression of the cell surface components to which the compounds described herein bind. Due to the differential numbers of binding sites on viable cells as compared with early-apoptotic, late-apoptotic and/or necrotic cells (viable<early-apoptotic<late-apoptotic/necrotic), the present invention allows for the design of buffers capable of blocking compounds described herein from binding to viable cells so as to enhance specific targeting of non-viable, i.e. dying and dead, cells.

In one embodiment, the methods provided by this invention may optionally comprise a step, for example a first step, in which a cell population such as a cell culture is contacted with a blocking buffer comprising one or more blocking molecules. A blocking molecule may be any molecule, which prevents, inhibits or competes with the non-proteinaceous compounds described herein, for binding to viable cells. Viable cells may comprise a variety of different moieties (for example cell surface components) capable of binding the non-proteinaceous compounds provided by this invention and some of these moieties may also be present on non-viable cells. In some cases, certain forms of moiety capable of binding the non-proteinaceous compounds provided by this invention may not be present on non-viable cells.

In one embodiment, the blocking molecules are soluble molecules which may interfere, inhibit or compete with the ability of a polysaccharide such as, for example dextran, to bind to viable cells. As such, a blocking molecule may bind polysaccharide binding moieties, for example dextran binding moieties, present on viable cells. These, or other polysaccharide (for example dextran or modified dextran) binding moieties may also be present on non-viable cells, but in greater numbers.

By preventing the non-proteinaceous compounds provided by this invention (for example dextran or modified dextran) from binding to viable cells, it may be possible to reduce the number of viable cells removed from a cell population when executing the methods described herein.

The term "blocking molecule" may be taken to relate to any of the non-proteinaceous compounds provided by this invention, formulated at a concentration to block all (or substantially all) the cell surface components which bind said non-proteinaceous compounds and which are present on viable cells, but leave a number of the non-proteinaceous compound-binding sites present on, or in, non-viable cells, exposed or unblocked.

By using a blocking buffer, when non-proteinaceous compound of the invention is added to the cell culture, only the non-viable cells with exposed (or unblocked) cell components capable of binding the compound, bind thereto. By adding non-proteinaceous compound to cell cultures in the form of a recoverable particle as described herein, it is possible to reduce the number of viable cells removed—as the blocking buffer will prevent compound binding thereto.

It should be understood that a blocking buffer or blocking molecule(s) may be added to a cell population together with any of the non-proteinaceous compounds provided by this invention. Additionally, or alternatively, the blocking buffer or molecule(s) may be added separately before, or after, the addition of the non-proteinaceous compounds described herein. As such, in one embodiment, the method of removing non-viable cells from a cell population provided by this invention comprises the step of contacting a cell population with a composition comprising one or more blocking molecules and a non-proteinaceous compound described herein, under conditions suitable to permit binding between the non-proteinaceous compound and any non-viable cells present in the cell culture and removing at least some of the non-proteinaceous compound from said cell population. In other embodiments, the methods provided by this invention include a separate step—executed either before or after a cell population is contacted with a non-proteinaceous compound described herein, said separate step comprising contacting the cell population with a blocking buffer or blocking molecule(s). In one embodiment, the blocking buffer or blocking molecule(s) may be contacted with the cell population under conditions suitable to permit binding between the blocking molecule(s) (of the blocking buffer) and viable cells which comprise moieties capable of binding said blocking molecules.

In one embodiment, a blocking buffer of this invention comprises 0-50%, 0-40%, 0-30% or 0-20% dextran as described herein. In a further embodiment, a blocking buffer may comprise 0-10% dextran such as, for example, 0%, 1%, 2%, 4%, 6%, 8% or 10%. It should be understood that the term "dextran" encompasses all forms of dextran (including modified forms) described herein.

Additionally, or alternatively, a blocking buffer may comprise a proteinacious composition or compound such as for example, serum or serum albumin. In one embodiment, a blocking buffer may comprise bovine serum albumin (BSA). Blocking buffers provided by this invention may comprise 0-50% serum or serum albumin. In one embodiment, blocking buffers may comprise 0-45%, 0-40%, 0-35%, 0-30% or 0-25%. In some embodiments, blocking buffers may comprise 0-10% serum or serum albumin (for example BSA). For example, blocking buffers may comprise 0%, 1%, 2%, 4%, 6%, 8% or 10% serum albumin (for example BSA).

In yet further embodiments, blocking buffers may comprise serum, for example, foetal calf serum (FCS). Serum may be added to blocking buffers described herein to a final concentration of, for example, 0-50%, 0-40%, 0-30% or 0-20%. In some embodiments blocking buffers may be supplemented with serum to a final concentration of 0-10%. In some embodiments, blocking buffers may comprise 0%, 0.25%, 0.5%, 1% 2%, 4%, 6%, 8% or 10% serum.

In other embodiments, blocking buffers described herein may additionally or alternatively comprise glucosamine. In certain embodiments, blocking buffers may comprise 0-50%, 0-40%, 0-30%, 0-20% or 0-10% glucosamine. For example, blocking buffers may comprise 0%, 0.25%, 05%, 1%, 5% or 10% glucosamine.

In one embodiment, a blocking buffer comprises BSA and dextran.

By altering the precise concentration of the blocking molecules of the blocking buffer it may be possible not only exclude or minimise the removal of viable cells, but also dying (including for example apoptotic) cells. One of skill will appreciate that a buffer formulated to block non-proteinaceous compound of this invention binding to viable cells may comprise a lower concentration of a non-proteinaceous compound capable of binding non-viable cells than a buffer formulated to block binding of the compound to viable and dying cells (which express more cell surface components capable of binding non-proteinaceous compound than viable cells, but less than dead or necrotic cells).

In addition, the methods provided by this invention may be further modified to include steps in which the environment of a cell population is modulated. For example, the methods described herein may include steps which modify environmental conditions such as, for example, temperature, pH, osmolarity, availability of one or more factors (for example small organic molecules or the like, proteins, peptides and/or amino acids) and/or overall charge of a cell population. By way of example, in order to modulate charge, further protein may be added to a cell population. It is to be understood that by altering environmental conditions such as, for example, the net charge of a cell environment, it may be possible to influence the number of cell components capable of binding the compounds described herein, present on viable and non-viable cells. Accordingly, such modifications provide a further means of altering the number of viable cells retained in a cell population following execution of the methods described herein.

For example, the methods provided by this invention may be conducted at low or acidic pH in order to enhance selectivity for non-viable cells. In one embodiment, the methods may be conducted at approximately pH 7.4, approximately pH 7 or approximately pH 6.6.

It should be understood that a method in which only dead cells (and not dying cells) are removed from cell cultures might provide further advantages over the prior art. As stated, cell populations such as cell cultures may comprise dying cells and these may take the form of apoptotic cells which are in the process of undergoing programmed cell death. Cells which are in the early stages of apoptosis are known to produce a number of growth factors, including lactoferrin, which have a positive effect on surrounding viable cells. Any method which leaves dying cells in cell cultures such that viable cells benefit from the growth factors produced thereby has distinct advantages.

In addition, to providing methods which facilitate the removal of non-viable cells from cell cultures and the like, the present invention and in particular the finding that non-viable cells possess more cell components capable of binding the compounds described herein, than viable cells, has a number of uses.

In particular, a second aspect of this invention provides the use of a compound described herein, for removing non-viable cells from cell populations such as, for example cell cultures.

In one embodiment, the compound for use in the second aspect of this invention is not a protein.

Additionally, the methods and uses described herein may find particular application in methodologies used to establish cell lines. One of skill in the field of cell culture would understand that when trying to establish a cell line, it is often difficult to selectively propagate a particular cell type from a mixed population which comprises large numbers of non-viable cells. Furthermore, the prolonged and continual culture of cells over numerous passages can often lead to the accumulation of high numbers of non-viable cells which may negatively impact upon the viability and productivity of the cell culture. By supplementing methods used to generate or establish cell lines with the methods described herein and thus exploit the use of the compounds of this invention to remove non-viable cells from cell cultures, it may be possible to facilitate the establishment of particular cell lines.

In addition to the above, the polymers and methods described herein may find further use in methods of cell storage and/or transport. It will be appreciated that stored cells are prone to die, particularly cells stored for prolonged periods of time or subject to freeze/thaw cycles. The accumulation of non-viable cells in stored cell cultures may decrease the overall viability of the stored cell culture and thus it is desirable to remove non-viable cells. Similarly, cells in transit may die—especially when transported in cold (i.e. 4° C.) and not frozen (−20° C. or −80° C.) conditions for prolonged periods of time. Under these conditions, the use of a compound to remove non-viable cells or method for achieving the same is particularly advantageous.

Methods of establishing primary cell cultures—i.e. cell cultures obtained directly from tissue samples, explants and/or biopsies, may also benefit from the methods and/or uses described herein. In particular, by removing non-viable cells from developing primary cell cultures, the overall efficiency of primary cell culture establishment may be improved to yield cultures which comprise high proportions of viable cells.

It is known that the success, efficiency or accuracy of cell-based assays can often suffer as a result of background levels of non-viable cells present in such assays. Advantageously, the methods and uses provided by this invention may be further exploited to remove non-viable cells from cell-based assay systems and decrease, reduce or eliminate background activity and/or the level or number of non-viable cells present.

In view of the above, it will readily be understood that the methods and uses provided by this invention may be further exploited as a means of improving the efficiency of transfection techniques such as electroporation, heat shock and or chemical transfection. Since only viable cells are capable of taking up nucleic acid, the efficiency of any given cell transfection technique may be greatly improved by increasing the proportion of viable cells present in a cell culture. As such transfection methodologies may be further supplemented with the methods described herein or with the use of a compound provided by this invention, to improve or increase transfection efficiency (i.e. the number of cells successfully transfected following execution of a transfection protocol).

In addition to the above, methods aimed at generating or yielding cell products, such as proteins (especially recombinant proteins) and/or nucleic acids (for example RNA or DNA) may be greatly improved by removing non-viable cells. Furthermore the quality of the cell product may also be improved. Indeed, by supplementing, for example, RNA extraction methods with the methods and/or uses described herein, it may be possible to yield protocols which result in the preparation of perfectly intact RNA (RNA integrity number (RIN) of 10).

Since the compounds described herein have been found to selectively or preferentially bind to non-viable cells, they may easily be exploited as a means of identifying, labeling or tagging dying or dead cells.

Thus in a third aspect, the presenting invention provides the use of a compound described herein for labeling or tagging non-viable cells.

In one embodiment, the compounds described in this invention may be further modified to include some form of detectable tag. By way of example, the compound may be conjugated or bound to (or otherwise associated with) an enzyme capable of reporting a level via a colourimetric or chemiluminescent reaction. Such conjugated enzymes may include but are not limited to Horse Radish Peroxidase (HRP) and Alkaline Phosphatase (AlkP). Additionally, or alternatively, the polymer compound may be conjugated to fluorescent molecules such as, for example fluorophores, such as FITC, rhodamine or Texas Red. Other types of molecule which may be conjugated to compounds of this invention include, for example, green fluorescent protein (GFP), radiolabelled moieties and the like. Compounds described in this invention may also be labelled with contrast agents suitable for use in ex vivo, in vivo or medical imaging techniques.

In order to label or tag non-viable cells, tagged or labelled compounds may simply be added to cell populations such as cell cultures under conditions suitable to permit binding between the tagged or labelled compound and any non-viable cells present in the cell culture.

Accordingly, in a fourth aspect, there is provided a method of labelling, tagging and/or identifying non-viable cells, said method comprising the steps of:
(a) contacting a cell population such as a cell culture with an optionally modified (i.e. tagged or labelled) compound described herein under conditions suitable to permit binding between the compound and any non-viable cells present in the cell culture;
(b) removing unbound compound; and
(c) detecting cells bound to the compound
wherein, cells bound to the compound comprise non-viable cells.

One of skill in this field will understand that having tagged or labelled a non-viable cell with a modified compound provided by this invention, techniques such as fluorescence microscopy may be used to detect the modified (i.e. tagged or labelled) compounds bound to dead and/or dying cells.

Unbound compound may be removed in a number of ways. In the first instance, unbound compound may be removed by repeated washing with buffer solutions. Other methods of removing unbound compound may include, for example the use of filtration (i.e. exploiting the fact that compound bound to cell(s) may be larger than unbound compound) and/or density separation techniques such as centrifugation.

Since the inventors have discovered that the number of compound binding sites present on and/or in cells increases as cells die and that, a degree of binding to viable or dying cells may also occur, to reduce the number of viable and/or dying cells labelled, tagged or identified, it may be beneficial to include an additional first step in which the cell culture is first contacted with a blocking buffer as described above. In this way, when subjected to the method provided by the fourth aspect of this invention, only dead cells (and not dying cells) may be labelled, tagged and/or identified.

One of skill will appreciate that since apoptotic cells may express more cell surface components capable of binding the compounds described herein than viable cells (but less than dead cells), it may be possible to further modify the methods provided by the fourth aspect of this invention to ensure apoptotic cells, as well as dead cells are labelled, tagged and/or identified. By way of example, by contacting a cell population with a blocking buffer formulated to include a concentration of compound effective to block all (or substantially all) the cell surface components capable of binding the compounds of this invention on viable cells but leave binding sites exposed or unblocked on dying, apoptotic and/or dead cells, it may be possible to provide a method in which apoptotic cells are also tagged, labelled and/or identified.

The compounds described herein—particularly modified (tagged or labelled) compounds, may be used in in vivo and/or in vitro imaging techniques to detect or view non-viable cells. By way of example, a compound provided by this invention may be modified to include some form of contrast agent detectable by ex vivo imaging means (MRI, CAT scan, X-ray or the like) and administered to a patient or a sample derived therefrom. By observing the patient or sample with suitable apparatus, it may be possible to obtain images of non-viable cells. Such images may be used in the diagnosis of a number of diseases.

In addition to the above, the observation that cell surface components capable of binding the compounds described herein increase during cell death (including apoptosis), may be exploited as a means of targeting particular compounds to dead or dying cells. Applications of this type may be particularly useful in the treatment of cell proliferative and/or differentiation disorders such as, for example, cancer.

Accordingly, a fifth aspect of this invention provides the use of a compound and/or modified compound provided by this invention for treating a cell proliferation and/or differentiation disorder.

In a sixth aspect, the present invention provides the use a compound and/or modified compound provided by this invention in the manufacture of a medicament for treating cell proliferation and/or differentiation disorders.

In a seventh aspect, the present invention provides a method of treating a cell proliferation and/or differentiation disorder, said method comprising the step of administering a therapeutically effective amount of a compound and/or modified compound provided by this invention to a patient in need thereof.

It should be understood that the term "compound" or "modified compound" as used in the fifth, sixth and seventh aspects above encompasses any of the (tagged or labelled) compounds described herein that are capable of binding non-viable cells. In one embodiment, the uses, medicaments and methods described herein may utilise polysaccharide, for example dextran (or carboxylated/amino dextran and/or modified dextran) compounds.

In an eighth aspect, the present invention provides a pharmaceutical composition comprising a compound and/or modified compound provided by this invention and a pharmaceutically effective excipient or diluent.

The medicaments and/or compositions provided by the $5^{th}$, 6th and $8^{th}$ aspects of this invention may be formulated as pharmaceutical compositions (preferably sterile pharmaceutical compositions) comprising a pharmaceutically acceptable carrier or excipient. Such carriers or excipients are well known to one of skill in the art and may include, for example, water, saline, phosphate buffered saline, dextrose, glycerol, ethanol, ion exchangers, alumina, aluminum stearate, lecithin, serum proteins, such as serum albumin, buffer substances such as phosphates, glycine, sorbic acid, potassium sorbate, partial glyceride mixtures of saturated vegetable fatty acids, water salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polypropylene-block polymers, polyethylene glycol and wool fat and the like, or combinations thereof.

One of skill will appreciate the medicaments and compositions described herein may be formulated for oral, parenteral, subcutaneous, intramuscular and/or intratumoural administration.

In one embodiment, the uses, compositions, medicaments and/or methods provided by the $5^{th}$-$8^{th}$ aspects of this invention may involve the formulation of a compound/modified compound for intratumoural administration of the modified compounds described herein.

In a ninth aspect, the present invention provides an in vitro method of targeting a compound of this invention to a non-viable cell, said method comprising the steps of contacting a population of cells with a modified compound (i.e. modified to include a further compound to be targeted to a non-viable cell) as described herein under conditions suitable to permit binding between the modified compound and any non-viable cells present in the cell population.

The term "cell population" should be understood as including cell cultures and/or cells derived from or present in tissue samples, biopsies and or explants.

By way of example, the modified compounds mentioned in the fifth, sixth, seventh, eighth and ninth aspects of this invention may comprise a drug, toxin, protein (such as an antibody or the like) and/or nucleic acid (for example antisense nucleic acid, microRNA, siRNA, iRNA and the like). More specifically, by providing modified compounds coupled or conjugated to, for example, anti-cancer, anti-tumour and/or cytotoxic compounds, it may be possible to deliver these compounds directly to non-viable cells present in, for example tumours. One of skill in this field will understand that by targeting non-viable cells within, for example a tumour, neighbouring viable and aberrantly proliferating tumour cells may become secondary targets of the compounds (for example cytotoxin, anti-tumour or anti-cancer compounds) conjugated or bound to the modified compounds.

In embodiments, where the compound takes the form of a recoverable particle (i.e. an iron-containing micro- or nanoparticle coated with a polymer compound) the targeting of compound (optionally modified to further comprise, for example, a protein, nucleic acid, drug, cytotoxin or anti-cancer or anti-tumour compound) to non-viable cells in tumours could be exploited as a means of killing or destroying neighbouring tumour cells by heat generation in a magnetic field. In addition, association of non-viable cells with such particles could lead to changes in the responses of phagocytes to these cells. In a tumour environment, this could be an alteration in the response of macrophages from pro-tumour to anti-tumour. Furthermore, engulfment of non-viable cells bound to compounds (optionally modified in accordance with this invention) could permit delivery of cytotoxic drugs to tumour-supportive macrophages or could allow targeted generation of heat in macrophages in order to kill them and thereby induce tumour regression.

Furthermore, the uses and methods described in the fifth-ninth aspects of this invention may be further supplemented with the use of a blocking buffer to block cell surface components capable of binding the compounds of this invention, present on cells (for example viable cells) not to be targeted by the modified compounds.

In a tenth aspect, the present invention provides a kit for the removal of non-viable cells from cell populations such as cell cultures, said kit comprising a compound provided by this invention and instructions for use. The kit may optionally contain buffers and reagents for use in the methods described herein, including, for example, blocking buffers formulated to provide compound at a particular concentration to prevent or minimise the removal of viable and/or dying cells from cell cultures.

DETAILED DESCRIPTION

The present invention will now be described in detail with reference to the following figures which show:

FIG. 1: Flow cytometric histograms demonstrating that dextran-FITC binds to viable and dead (necrotic) cells but with stronger intensity to dead cells. This was demonstrated by fluorescence labelling of viable and dead cells with dextran-FITC (dextran coupled to fluorescein isothiocyanate). Necrotic (dead) cells were generated by heat treatment (56° C., 1 hour; see [Devitt, 1998 #872]). Dotted line: background fluorescence; dashed line: 1 mg/ml dextran- FITC; solid line: 0.1 mg/ml dextran-FITC. A=% positive cells (1 mg/ml dextran FITC); B=% strongly positive cells (1 mg/ml dextran-FITC).

Figure 2:
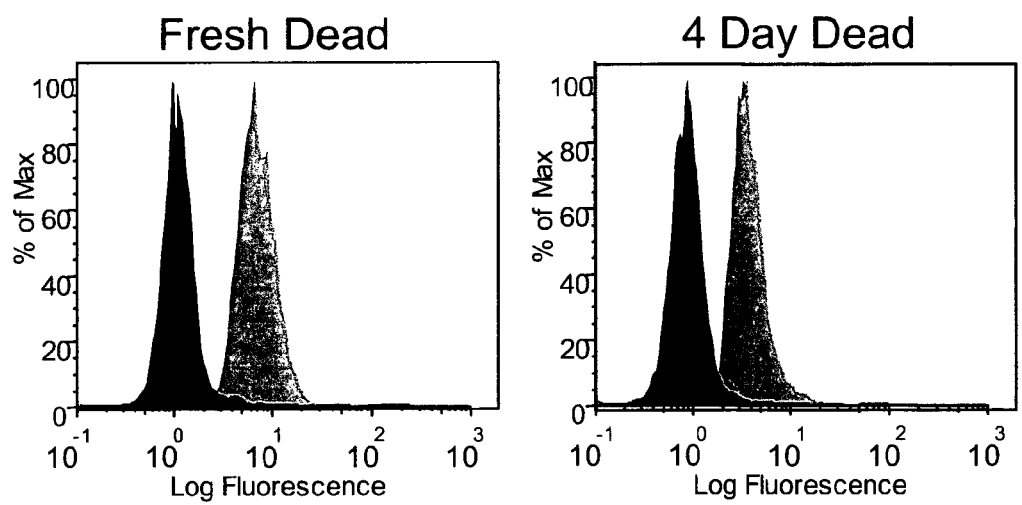

FIG. 2: As above, shows that dextran-FITC binds to viable and dead (necrotic) cells but with stronger intensity to dead cells. Black histograms: viable zone cells; grey histograms: dead zone cells.

Figure 3A:
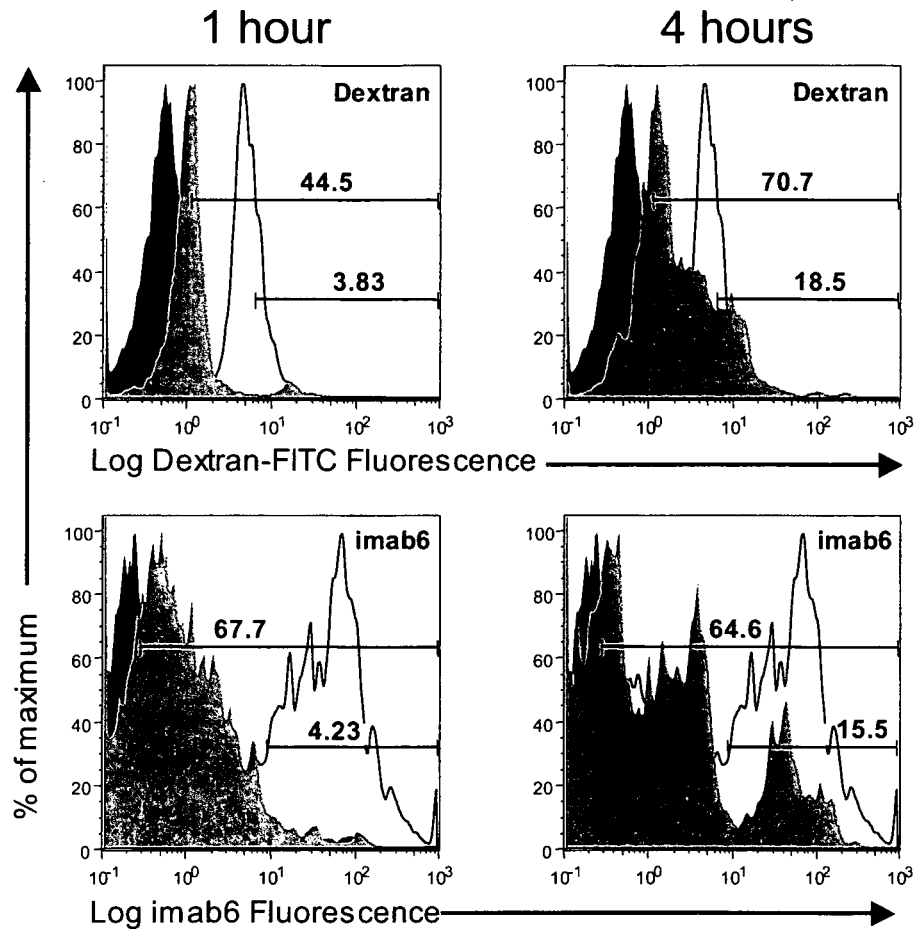

FIG. 3A: presents evidence that dextran-FITC detects apoptosis as well as secondary (post apoptotic) necrosis. Black histograms: propidium iodide (PI)-negative cells, 0 hours; grey histograms: PI-negative cells, 1 or 4 hours; open histograms, PI-positive cells, 0 hours. 3B: Scanning electron micrograph of amino-dextran nanoparticles binding to the surface of a dying fibroblast. L929 fibroblasts were cultured on glass coverslips until confluent then transferred to serum-free culture medium containing staurosporine (1 micro molar) for 3 hours to induce apoptosis after which they were exposed to 250 nm amino-dextran nanoparticles. Coverslips were then washed with PBS to remove unbound nanoparticles and fixed in 3% glutaraldehyde in a fridge overnight. They were dehydrated in ethanol in an EMS critical point dryer before mounting on stubs and sputter coating with osmium. Samples were examined and images recorded using a Phenom™ desktop scanning electron microscope (FEI Company). The nanoparticles can be clearly observed bound to discrete loci on the cell surface and its extensions.

Figure 4:
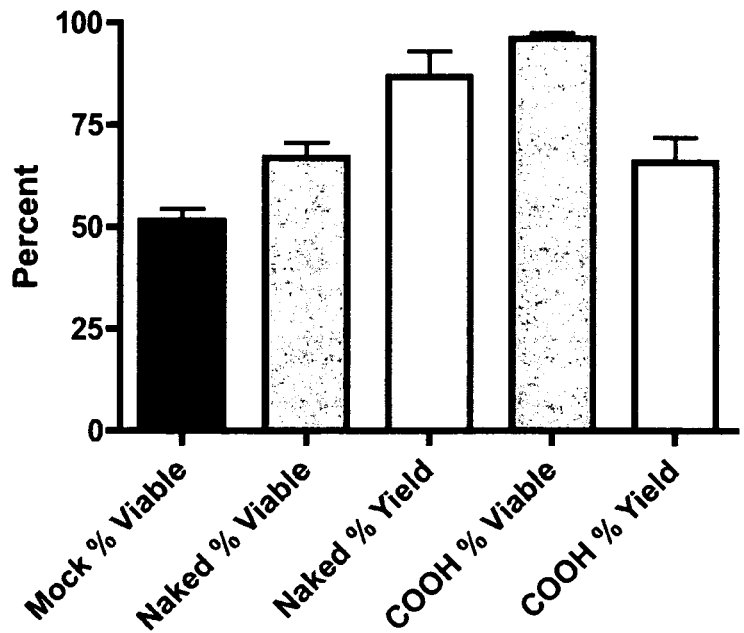

FIG. 4: Shows that primary necrosis occurs as a consequence of cells losing their plasma membrane integrity following a noxious treatment or injury without entry into apoptosis.

Figure 5:
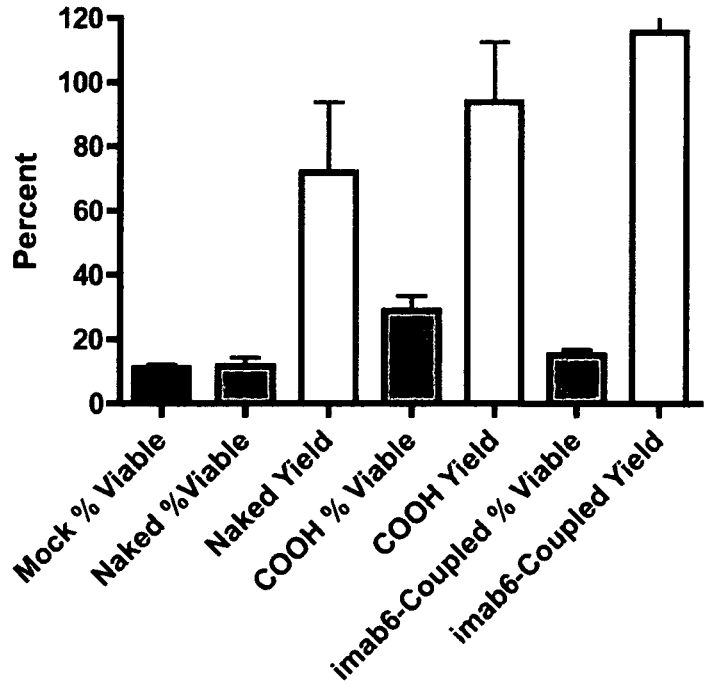

FIG. 5: Details improvements in viability of hybridoma cell cultures using carboxylated dextran-coated magnetic particles.

Figure 6:
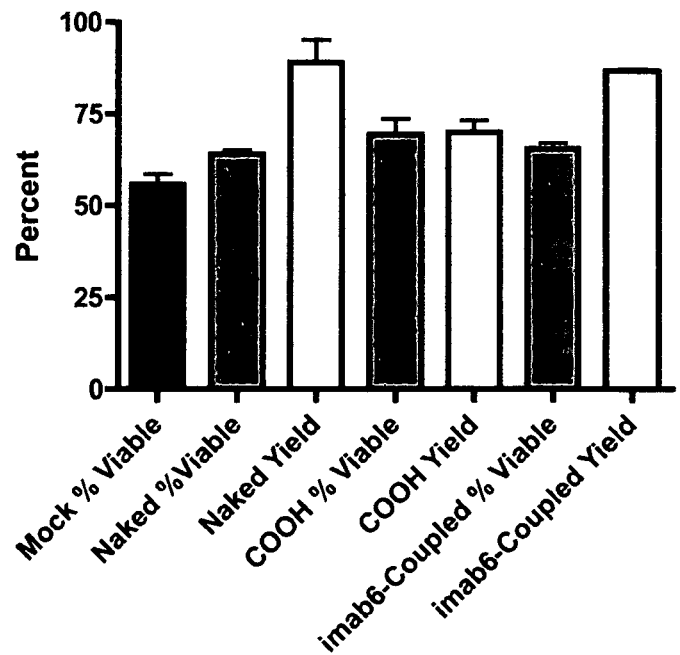
Figure 6:
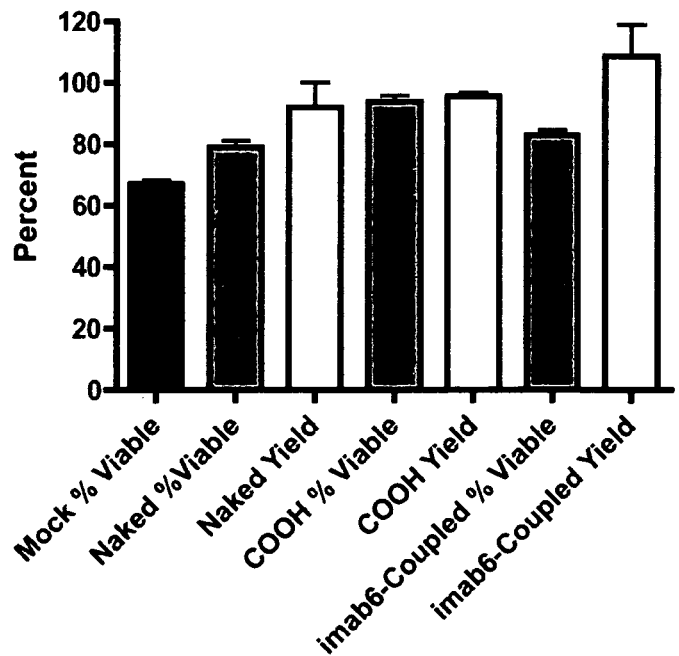

FIG. 6: As FIG. 5, also shows improvements in viability of hybridoma cell cultures using carboxylated dextran-coated magnetic particles FIG. 7: Shows the depletion of necrotic (heat-treated as described above) human B lymphoma cells from a mixture of ~2:1 necrotic:viable cells under various conditions.

Figure 8:
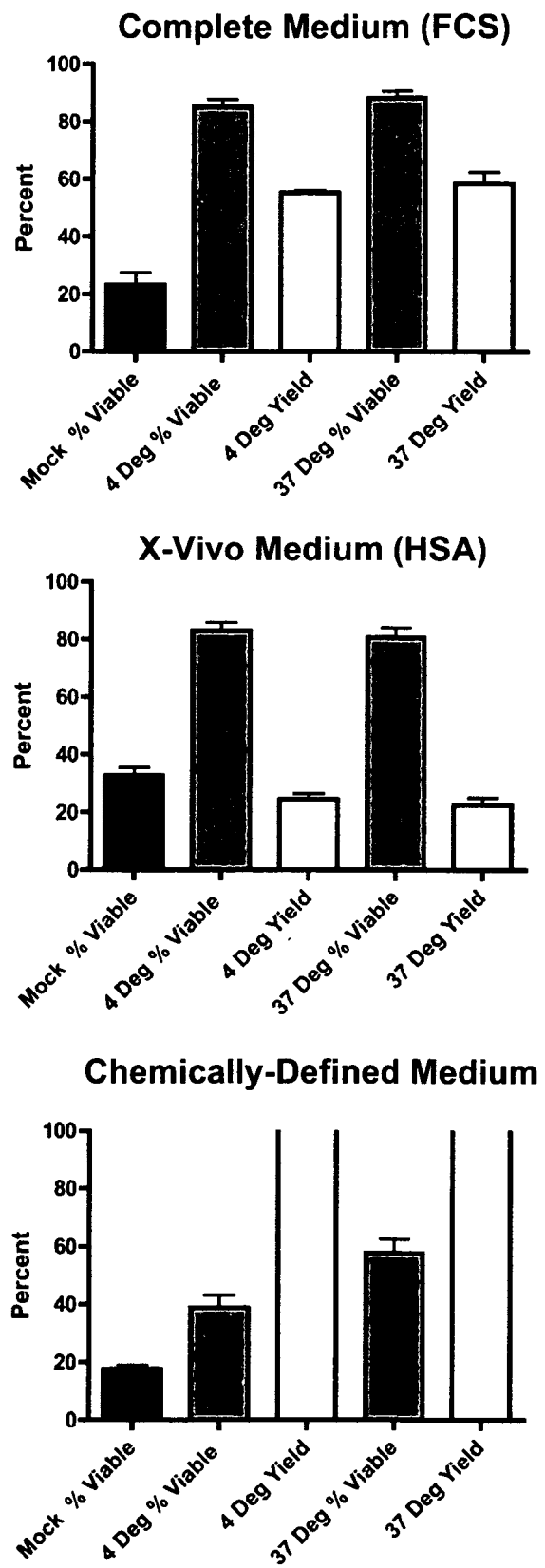

FIG. 8: presents further data showing the depletion of necrotic (heat-treated as described above) human B lymphoma cells from a mixture of ~2:1 necrotic:viable cells under various conditions.

Figure 9A:
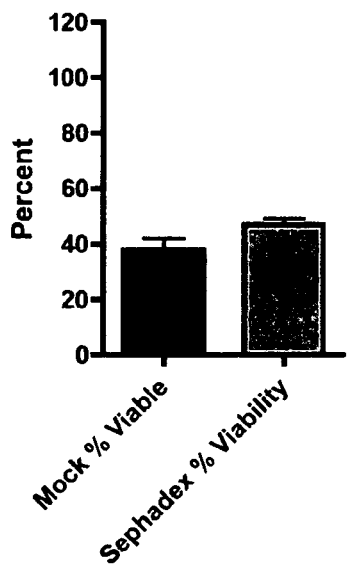
Figure 9B:
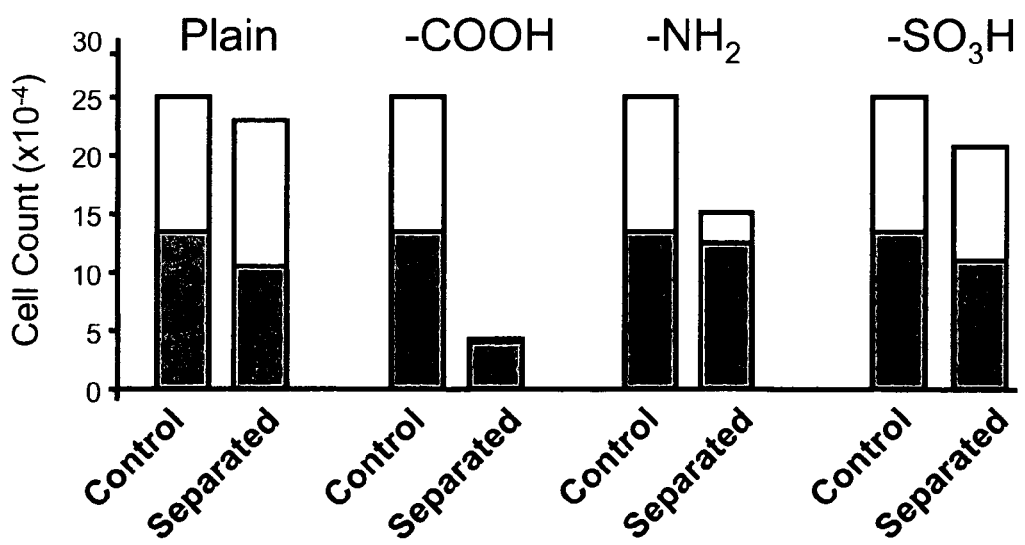
Figure 10A:
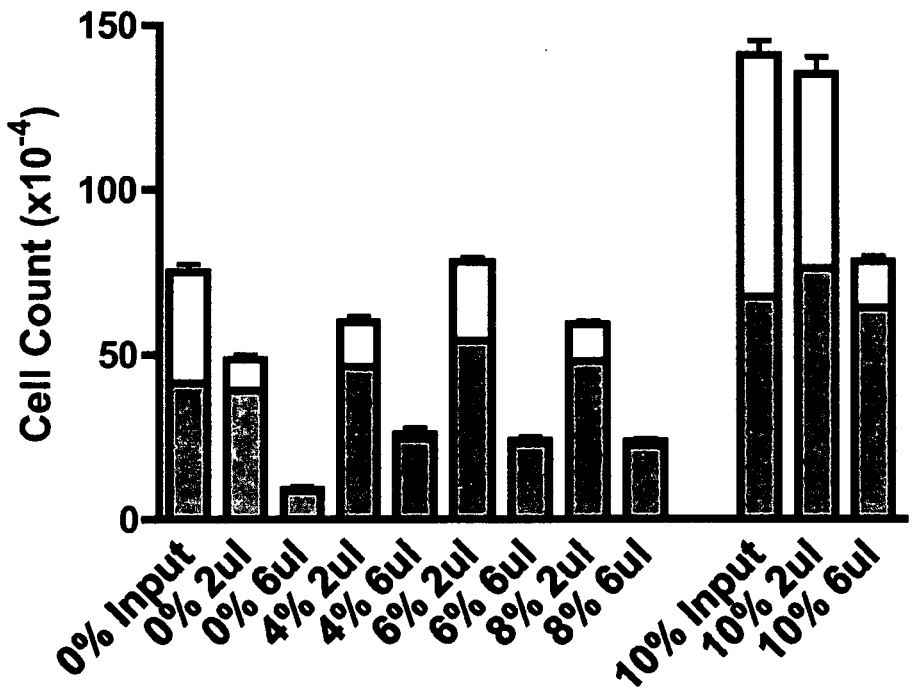
Figure 10B:
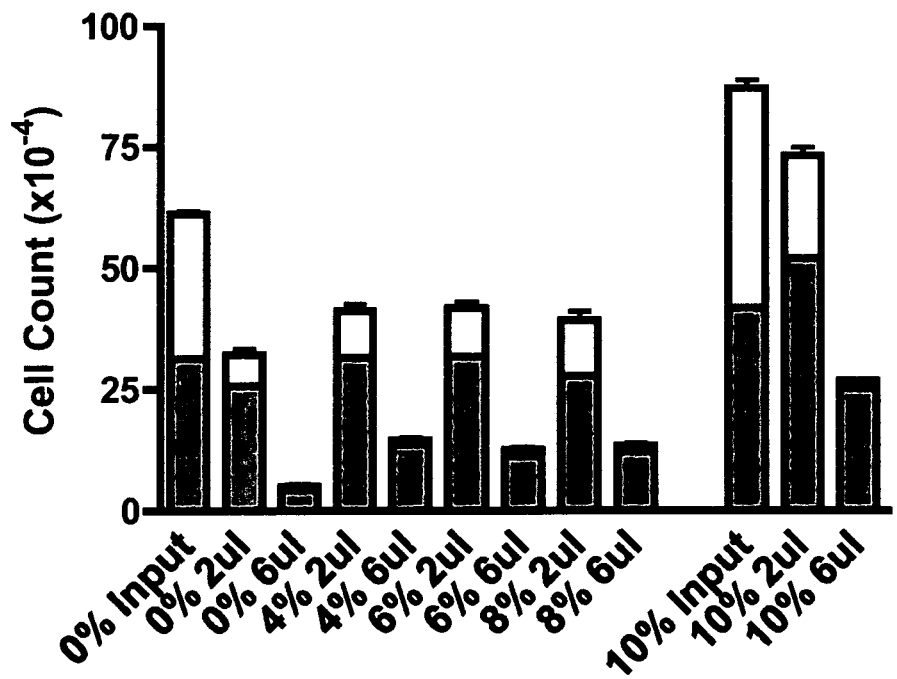
Figure 10C:
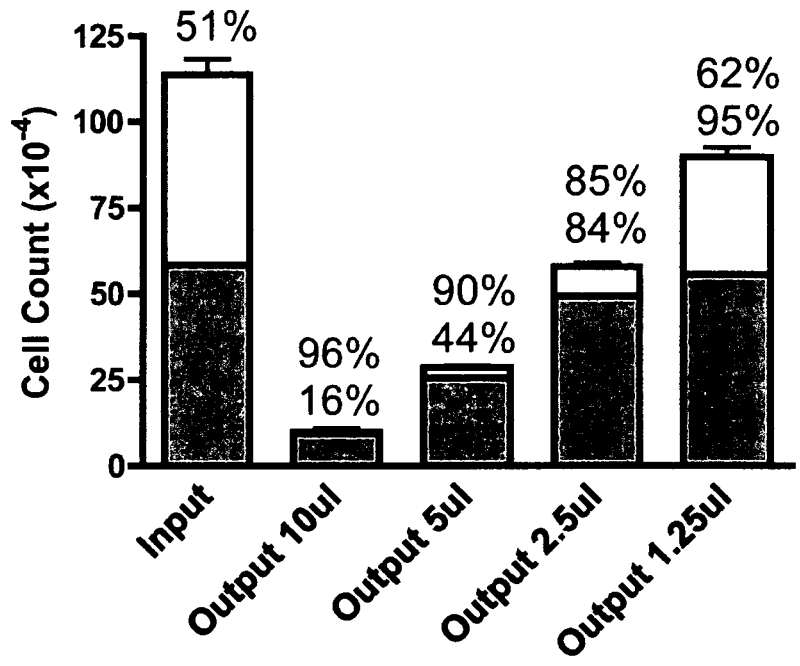
Figure 10D:
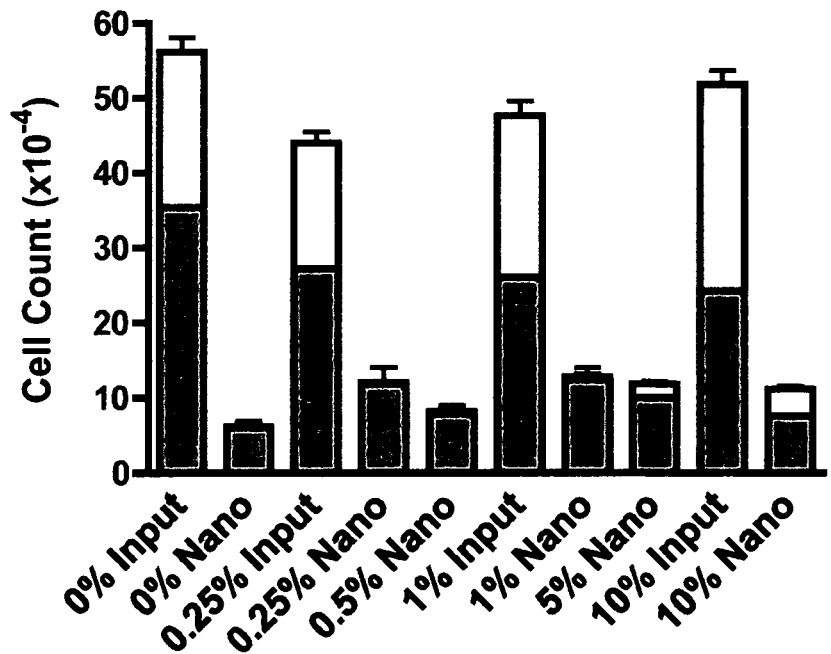
Figure 10E:
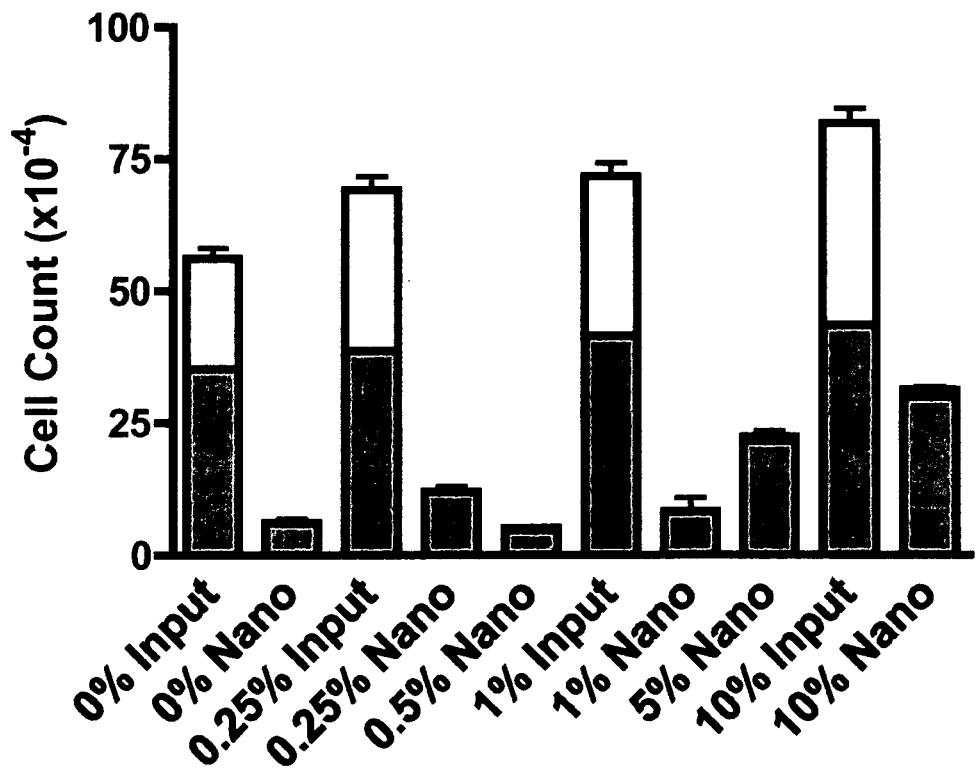

FIG. 9A: G-25 particles fail to significantly improve cell viability. Attempted depletion of necrotic (heat-treated as described previously) human B lymphoma cells from a mixture of ~2:1 necrotic:viable cells. Separation was attempted using 2 ml packed volume of washed Sephadex G-25 particles (85-260 µm, GE Healthcare) in complete culture medium (RPMI+10% FCS). Briefly, cells were incubated with G-25 (equilibrated with complete culture medium) for 90 minutes at 37° C. Subsequently, cells+ particles were resuspended in complete culture medium and cells recovered from particles following rapid 1 g settlement of particles. Following separation, triplicate haemocytometer counts of trypan blue-stained cells were performed and expressed as mean % Viable cells+SEM (black and blue bars). Mock=input cells (no particles included). 9B: Chemical modification of dextran particles to promote selective binding to non-viable cells. Cryo-damaged Chinese hamster ovary (CHO) cells were subjected to separation with superparamagnetic nanoparticles using the method as described in FIG. 4. Nanoparticles were coated either with plain dextran or dextran modified with the indicated chemical groups. Control=Input cells; Separated=Output cells. Viability counts were performed using Neubauer haemocytometer chambers and trypan blue exclusion. Grey bars are viable cell counts; open bars are non-viable cell counts. All separations were performed at 4° C. in RPMI medium containing 10% fetal calf serum (FCS). The results demonstrate that both —COOH— and —NH2-modified particles were superior in selective binding to non-viable cells. However, the latter proved more effective in this example at providing the best yield of viable cells with only low-level contamination by non-viable cells. These results exemplify the modification of dextran to facilitate selective targeting of non-viable cells.

FIG. 10: Controlling selective binding of dextran nanoparticles to non-viable cells by varying nanoparticle concentration and concentrations of soluble sugars or protein. Grey bars are viable cell counts; open bars are non-viable cell counts. A—Different doses of nanoparticles (2 or 6 µl stock) used to separate viable from non-viable cells in phosphate-buffered saline (PBS) containing varying concentrations of bovine serum albumin (BSA, 0-10%). Yield of viable cells is markedly enhanced in the presence of high numbers of nanoparticles by the presence of BSA. At lower nanoparticle concentration, the presence of the protein compromises efficiency. This example demonstrates that selective binding of dextran-coated nanoparticles to non-viable cells can be controlled by regulating particle numbers and protein concentration. B—Very similar example to FIG. 10A except that varying concentrations (%) of Dextran (MW 7,000) are used to inhibit binding of dextran-coated nanoparticles selectively to viable cells. C—Increasing particle/cell ratio improves efficiency of dead-cell removal but decreases yield of viable cells. Viability of Input population in this example was 51%; viabilities of output samples are given (upper percentages over Output bars) above % yield of viable cells (lower percentages over Output bars). Output yields were calculated as percentages of input numbers of viable cells. Regulation of particle numbers is a means to define optimal efficiency of separation and resultant yield of viable cells. Input=mock separation in the absence of nanoparticles and Output=separation in the presence of nanoparticles from stock at the indicated concentrations. D—Increasing glucosamine concentration selectively inhibits binding of nanoparticles to viable cells, but at highest concentrations begins to be inhibitory to binding of nanoparticles to non-viable cells. % indicates percentage of glucosamine in PBS present during the separation. 0% is PBS alone. Input=mock separation in the absence of nanoparticles and Nano=separation in the presence of nanoparticles. E—Increasing serum concentration selectively inhibits binding of nanoparticles to viable cells. % indicates percentage of fetal calf serum in PBS present during the separation. 0% is PBS alone. Input=mock separation in the absence of nanoparticles and Nano=separation in the presence of nanoparticles. In all cases, separations were carried out as described for FIG. 4 except that dextran particles were modified by the addition of amino groups. In each case "Input" is equivalent to "Mock" separation—i.e. treatment of cell populations in the absence of nanoparticles.

Figure 11:
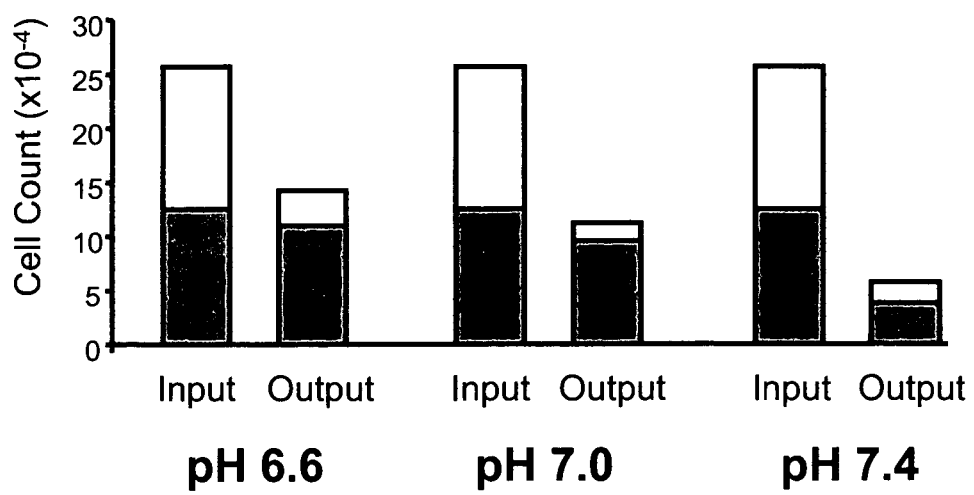

FIG. 11: Altering pH to control selective binding of nanoparticles to non-viable cells. CHO cells were subjected to separation (Output) or mock separation (Input) using superparamagnetic dextran particles modified by addition of amino groups. Non-viable cells were generated through cryo-damage. Separations (mock/Input="separation" in the absence of nanoparticles) were carried out in PBS containing 10% BSA at the indicated pH. Lowering of pH was found to promote selective removal of non-viable cells while reducing loss of viable cells (ie relative binding of particles to non-viable cells versus viable cells). Grey bars are viable cell counts; open bars are non-viable cell counts. This example demonstrates that manipulation of pH can be used to selectively target non-viable cells for removal by amino-dextran particles.

Figure 12:
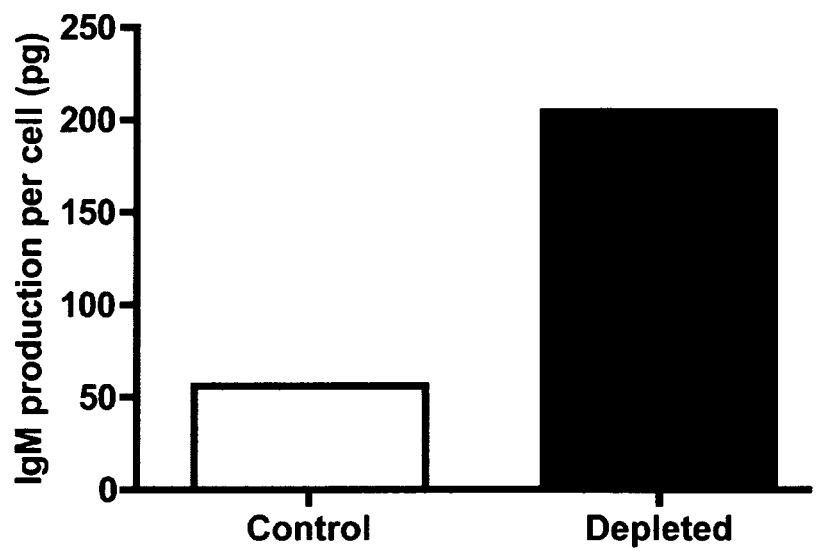

FIG. 12: Improved productivity of hybridoma, O4 in bioreactor culture after depletion of dead and dying cells by amino-dextran super-paramagnetic nanoparticles. The hybridoma produces anti-oligodendrocyte marker O4 antibodies of IgM class. Sommer, I. and Schachner, M., Monoclonal antibodies (O1 to O4) to oligodendrocyte cell surfaces: an immunocytological study in the central nervous system, *Dev. Biol.*, 83, 311-127 (1981). The hybridoma was resuscitated from a frozen stock and cultured for 24 hours in Dulbecco's Modified Eagle's Medium containing 10% foetal bovine serum and glutamine. At this stage the cells were only 2% viable on the basis of trypan blue permeability. The culture was divided and one fifth was subjected to fractionation using amino-dextran super-paramagnetic nanoparticles. The viability of the depleted cells was improved 7.5 fold to 15%. Depleted and untreated cells were cultured for a further 3 weeks as described above then for a further 7 days in protein-free CD Hybridoma medium (InVitrogen Ltd) supplemented with glutamine and cholesterol. Equal numbers of viable cells from each culture were transferred to a Celline CL350 bioreactor (Integra Biosciences AG). The viabilities were 69% and 73% for control and depleted cells respectively. After 5 days cell supernatants were collected and IgM concentrations measured. The IgM production per viable cell for each culture is given in the figure and was around 300% higher in the depleted culture than that of the untreated (Control) culture. These results demonstrate that dead-cells are inhibitory to the productivity of antibody-producing cells and that the removal of dextran-binding dead cells (though dead-cell removal was only partial in the face of such low viability) effectively removes inhibitory factions of the dead-cell population.

Figure 13:
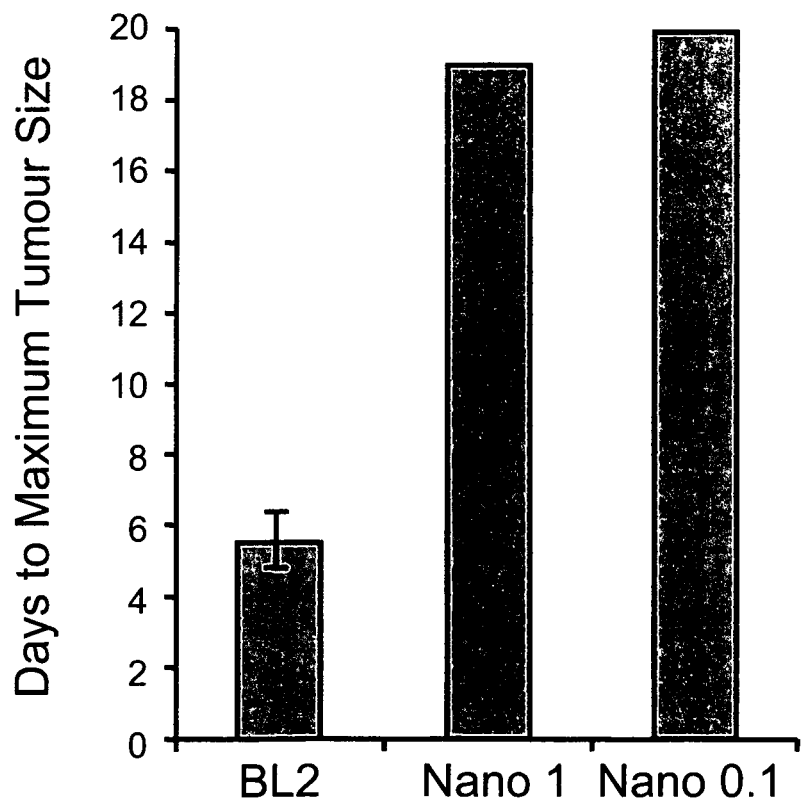

FIG. 13: Modulation of tumour growth in vivo by amino-dextran nanoparticles. SCID mice were injected subcutaneously with $10 \times 10^6$ human lymphoma cells (BL2) and the number of days post-detection of the tumour before it reached 14 mm in diameter (the maximal size permitted) were recorded. Left bar: mean±SEM, BL2 untreated (n=14 tumours). Middle bar: BL2 tumour injected intratumourally 3 days after detection with 50 µl (1 mg/ml) amino-dextran nanoparticles. Right bar: BL2 tumour injected intratumourally 3 days after detection with 50 µl (0.1 mg/ml) amino-dextran nanoparticles. Untreated tumours are typically "starry sky" in histological appearance indicative of high levels of apoptosis and macrophage infiltration. These results demonstrate that intratumoural injection of nanoparticles can significantly slow tumour growth, consistent with the notion that binding of dextran nanoparticles to dying or dead tumour cells alters the nature of the innate immune response (clearance activity by macrophages) in the tumour.

EXAMPLE 1

Dextran Binds to Both Viable and Dead (Necrotic) Cells, but with Stronger Intensity to Dead Cells (More Dextran Binding Sites on Dead Cells)

Human B-lymphoma cells, subjected to heat treatment to induce necrosis in the whole population (all cells trypan blue positive), were mixed with viable lymphoma cells in a ratio of ~1:1. Cells were then labelled with indicated doses of dextran-FITC (molecular weight 4,000; Sigma), washed, fixed in formaldehyde, and subsequently analysed by flow cytometry using an EPICS cytometer (Beckman-Coulter). Absissa: Log Fluorescence, Dextran-FITC. Light scatter parameters were used to discriminate 'Viable Zone' and 'Dead Zone' cell populations (see [Dive, 1992 #350]). Data is presented in FIG. 1. Note that, at 0.1 mg/ml, virtually no dextran-FITC fluorescence was observed above background amongst viable cells and only a small shift in fluorescence was found in the dead zone at this concentration. By contrast, at 1 mg/ml, >90% of viable and dead cells were positive (A gates). Of these, virtually all dead-zone cells were strongly dextran-FITC-positive (B gates) whereas virtually no viable-zone cells were strongly positive under these conditions.

Dextran-FITC Binds to Viable and Dead (Necrotic) Cells but with Stronger Intensity to Dead Cells: Extra Binding Sites on Dead Cells Retained for Extended Time Period.

Human B-lymphoma cells were heat-treated to induce necrosis as described in FIG. 1; dead cells were mixed in equal proportions with viable cells either immediately after heat treatment or after 4 days of further incubation at 37° C. Subsequently, the cell mixtures were labelled with 1 mg/ml dextran-FITC, fixed, and analysed by flow cytometry as before. As shown previously in FIG. 1, greater numbers of binding sites for dextran were found to be available on fresh dead cells compared with viable cells (FIG. 2: left panel), with approximately a log shift in fluorescence observed. After 4 days of culture under physiological conditions, dead cells continued to display substantially greater numbers of binding sites for dextran molecules as demonstrated by the stronger levels of fluorescence observed in virtually the entire population of dead cells (FIG. 2: right panel). It should be noted, however, that the differential fluorescence between viable and dead cell populations is lower at 4 days after death than immediately following the onset of necrosis.

These results demonstrate that dead cells can be differentiated from viable cells over an extended time period following necrotic death on the basis of differential display of accessible dextran binding sites.

EXAMPLE 2

Dextran Binding Sites are Increased Rapidly After the Onset of Apoptosis and, with Time, Achieve Levels Displayed by Necrotic Cells To study the effects of apoptosis on dextran binding sites, cells were induced to undergo apoptosis using the protein kinase inhibitor, staurosporine, a well-established apoptosis trigger. Cell death was monitored by flow cytometry following immuno-staining of cells using the anti-phospholipid antibody, Dead-Cert™imab6, which detects phospholipid changes on the surface of dying and dead cells (for further information see www.immunosolv.com/Apo-Technology.html and (national application GB 0723797.7). Dying cells (apoptotic) were further discriminated from dead cells (post-apoptotic; secondarily necrotic) using propidium iodide (PI), which is excluded from cells prior to the onset of necrosis (loss of plasma-membrane integrity).

Human B-lymphoma cells were induced to undergo apoptosis by treatment with 1 µM staurosporine and samples were taken from 1 to 5 hours after treatment. At the indicated times, cells were labelled with dextran-FITC as previously described and stained with PI (2 µg/ml) immediately prior to analysis of unfixed samples by flow cytometry. In parallel, samples were immuno-stained using Dead-Cert™imab6 (Immunosolv) and visualised using secondary goat anti-mouse Ig-FITC (Sigma). Imab6-labelled cells were also stained with PI prior to flow cytometry. Green (FITC) fluorescence histograms were generated for gated PI positive and PI negative cell populations. Within the PI-negative (non-necrotic) cell populations, levels of 'Total' and 'High' dextran or imab6 labelling were assessed. Data is presented in FIG. 3.

Figure 3B:
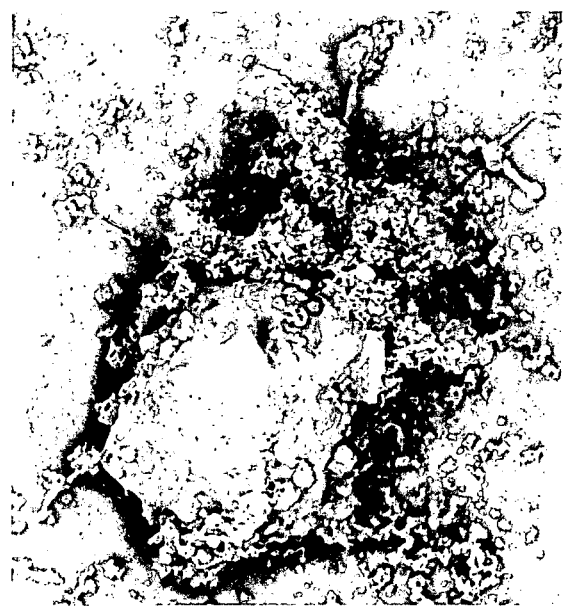

As shown in the upper left histogram panel (FIG. 3), a rightward shift in dextran-FITC fluorescence was observed in PI-negative, apoptotic cells (compare green with blue histograms) in the first hour following apoptosis induction. This was paralleled by a substantial shift in imab6 fluorescence of these cells (FIG. 3: lower left panel). Reference to the table summary (Table 2) indicates that, at this time, 45% of PI negative cells bound dextran compared with 68% that bound imab6.

TABLE 2

Percentages of fluorescent dextran-labelled lymphoma cells as measured by flow cytometry.

|      | % Dextran +ve | | % Imab6 +ve | |
| --- | --- | --- | --- | --- |
| Time | Total | High | Total | High |
| 0    | 6  | 1  | 28 | 3  |
| 1 h  | 45 | 4  | 68 | 4  |
| 2 h  | 57 | 2  | 86 | 6  |
| 3 h  | 77 | 7  | 79 | 6  |
| 4 h  | 71 | 19 | 65 | 16 |
| 5 h  | 62 | 27 | 50 | 24 |

Cells were labeled after exposure to the apoptosis-inducing agent staurosporine for the indicated times. All cells analysed were propidium-iodide negative and therefore, because their plasma membranes have not been permeabilised, the dextran is bound to the cell surface of apoptotic (dying) cells. Comparison is made between cells binding fluorescent dextran and the monoclonal antibody Imab6, which binds apoptotic cells. Total=all positive cells (above background fluorescence); High=strongly fluorescent cells. Examples of flow cytometric histograms are given in FIG. 3A.

Virtually no PI negative cells at the 1 hour time point were high binders of either dextran or imab6 (see FIG. 3: left panels and FIG. 3: table 1). By 4 hours, however, significant numbers of PI negative, apoptotic cells were found to display high levels of dextran fluorescence (FIG. 3: top right histograms and table), which were comparable to the high levels of imab6 labelling observed (FIG. 3: lower right histograms and table). Such high levels of fluorescence were also comparable to the levels found in PI positive cells (compare with red histograms—note that levels of green fluorescence in PI positive cells were closely similar at all time points—not shown). With reference to the table, note that, within the PI negative population, total percentages of dextran positive and imab6 positive cells rise, peak and fall within the 5-hour period studied. By contrast, the percentages of cells showing high fluorescence for each of these labels continue to rise beyond the times of peak percentages of total fluorescence, strongly suggesting that cells initially displaying relatively low fluorescence labelling, progress—along with the progression of apoptosis—to a strong dextran and imab6 labelling phase, prior to loss of membrane integrity.

These results demonstrate that dextran can be used to discriminate between viable, dying (apoptotic) and dead (necrotic) cells. Furthermore, the level of binding of dextran can be used as an indication of the phase of apoptosis: intermediate binding levels indicate early stages in the apoptosis programme whereas strong binding levels indicate late stages, both before and after loss of plasma membrane integrity.

EXAMPLE 3

Dextran Coated Particles can be Used to Remove Dead Cells in Vitro for a Variety of Applications Depletion of dead cells is important for numerous applications, including improving productivity of cells in culture, reducing background noise in cell-based assays, improving cell selection and cell-line establishment, improving quality of RNA and protein for biochemical applications, and extending the shelf-life of cells (for example therapeutic cells) during delivery to patients. Because dextran can be used to discriminate between viable, apoptotic and dead cells, this polymer has significant potential to be used as a protein-free tool (and therefore highly amenable to GMP applications) to separate dead cells from viable cells in order to produce viable cells in high purity for multiple applications. Furthermore, dextran has the potential to be used in separations designed to 'spare' early apoptotic cells since dextran binding sites, as demonstrated above, do not reach high levels until relatively late stages in the apoptosis programme. This may be particularly important in certain applications since early apoptotic cells have beneficial properties, including production of growth factors such as lactoferrin.

In order to investigate whether the enhanced binding of dextran to non-viable cells can be applied to cell separation, superparamagnetic particles consisting of core magnetite surrounded by a shell of dextran were tested under various conditions. In these examples, particles of 250 nm were used and were separated using a simple magnet.

Dextran Particles can be Used to Markedly Improve Viability of Cell Suspensions Containing Dead Cells Resulting from Primary Necrosis Primary necrosis occurs as a consequence of cells losing their plasma membrane integrity following a noxious treatment or injury without entry into apoptosis.

Human B-lymphoma cells, subjected to heat treatment to induce necrosis in the whole population (all cells trypan blue positive), were mixed with viable lymphoma cells in a ratio of ~1:1. Cells ($2.5 \times 10^6$) were incubated with 250 nm dextran coated superparamagnetic particles (10 µg, Micromod, either 'naked" particles (ie unmodified) or particles to which COOH groups had been added by the manufacturer) in 200 µl complete culture medium in an eppendorf tube for 55 minutes at 37° C. After incubation, the cells and particles were resuspended in 1 ml following the addition of 0.8 ml culture medium to the tube. Mock-separated cells were treated identically except no magnetic particles were included. Viability counts of Mock-separated cells were identical to untreated (input) cells. Tubes containing particles+cells were placed on a simple magnet (Immunosolv, DC-M1) for 3 minutes after which the particle-free cell suspension was removed and viability counting of trypan blue-stained cell populations performed using a Neubauer haemocytometer. Triplicate counts were performed and expressed as mean % Viable cells+SEM (black and blue bars). Yield of viable cells isolated is expressed as a percentage of the absolute number of input (mock-separated) viable cells. Data is presented in FIG. 4.

FIG. 4 demonstrates that effective depletion of necrotic cells can be obtained by simple binding of magnetic dextran particles to the dead cells followed by rapid magnetic separation of the particles, bound and non-bound. In this example, carboxylated (COOH) particles worked more effectively than 'naked' particles (improvement in viability from ~50% to almost 100%), although the yield of viable cells was lower with carboxylated particles.

Dextran Particles can be Used to Improve Viability of Cell Suspensions Containing Dead Cells Resulting from Apoptosis Cell death as a consequence of apoptosis leads to post-apoptotic necrosis—plasma-membrane breakdown following apoptosis, a process that is often referred to as secondary necrosis. Such cells do not normally persist in vivo because of the activity of phagocytes that efficiently remove apoptotic cells prior to loss of plasma membrane integrity.

A suspension of murine hybridoma cells of very low viability was obtained by neglect (cells undergo apoptosis in the absence of nutrients/growth factors) and separated using magnetic particles according to the regime described above with modifications: incubation of cells with particles was carried out for 45 minutes at ambient temperature (~20° C.). Unmodified particles (Naked) were compared with carboxylated particles (COOH) and particles covalently coupled to imab6. Following magnetic separation, triplicate haemocytometer counts were performed and expressed as mean % Viable cells+SEM. Yield of viable cells isolated is expressed as a percentage of the absolute number of input (mock-separated) viable cells. Data is presented in FIG. 5.

In this example (see FIG. 5), the very low viability of the hybridoma culture was enhanced more than two-fold using carboxylated particles which proved more effective than either naked or imab6-coupled particles.

As shown in FIG. 6, Human lymphoma cells were induced to undergo apoptosis by treatment with puromycin (2 μg/ml) or staurosporine (1 μM) for 18 hours after which the drug-induced apoptotic cells were washed and mixed with viable cells in approximately equal proportions. Separations were then carried out using dextran-coated magnetic particles which improved viability of populations containing either puromycin-treated or staurosporine treated cells. Carboxylated particles proved most effective (FIG. 6).

Dextran Particles can Remove Dead Cells with High Efficiency at Low Temperature and Under Conditions that are Free of Serum, Protein and Divalent Cations In order to exemplify the versatility of dextran for dead cell removal, separations were carried out under different conditions: at 4° C., 37° C., under serum and protein-free conditions and in the absence of $Ca^{2+}$ and $Mg^{2+}$ (low temperature separations may be preferred for preparation of cells in gene expression studies; physiological conditions for delicate cells; serum or protein-free conditions for therapeutic applications; $Ca^{2+}$ and $Mg^{2+}$ can cause cell clumping that is well known to markedly effect the efficiency of cell separations).

Depletion of necrotic (heat-treated as described above) human B lymphoma cells from a mixture of ~2:1 necrotic:viable cells under various conditions. Separations were carried out using carboxylated dextran-coated super-paramagnetic particles as described earlier with variations: separations were carried out either in complete culture medium (RPMI+10% FCS) or in $Ca^{2+}$-free and $Mg^{2+}$-free phosphate buffered saline (PBS) at 4° C. or 37° C. Data is presented in FIG. 7.

Figure 7:
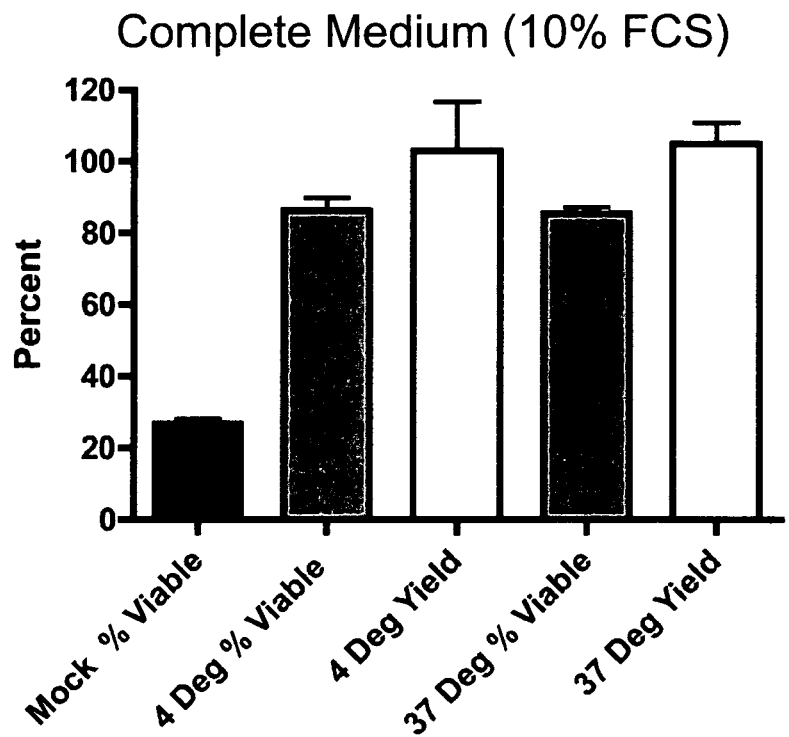
Figure 7:
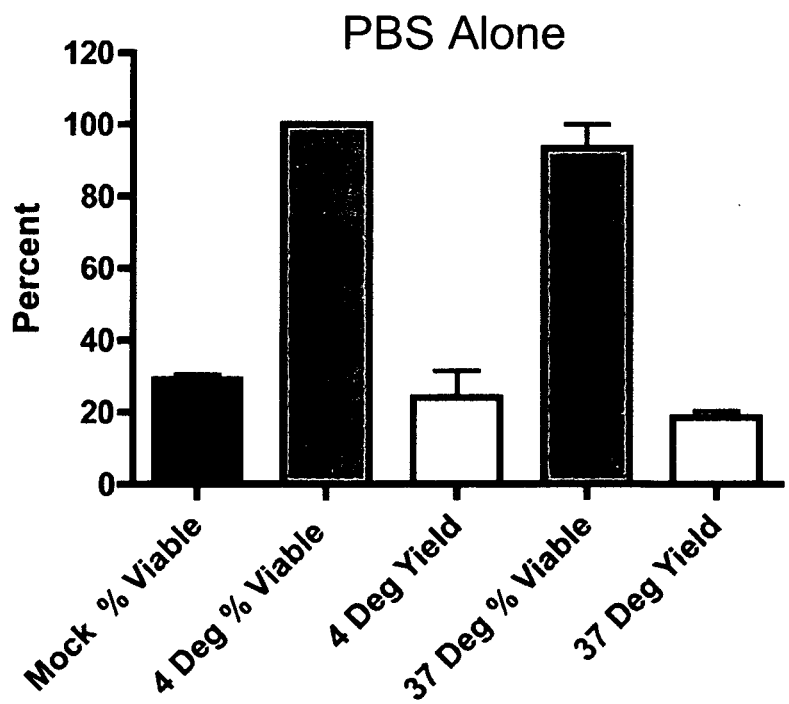

Following magnetic separation, triplicate haemocytometer counts of trypan blue-stained cells were performed and expressed as mean % Viable cells+SEM (FIG. 7: black and blue bars). Yield of viable cells isolated is expressed as a percentage of the absolute number of input (mock-separated) viable cells. This example (FIG. 7) demonstrates that highly efficient dead-cell depletion—such that viability can be enhanced from <30% to almost 100%—can be carried out in the cold or at physiological temperature either in complete culture medium (left panel) or in a simple buffer such as $Ca^{2+}$-free and $Mg^{2+}$-free PBS (FIG. 7: right panel). In this example, while highest efficiencies of purification of viable cells at either temperature were obtained using PBS, optimal yields were observed using complete culture medium.

Depletion of necrotic (heat-treated as described above) human B lymphoma cells from a mixture of ~2:1 necrotic:viable cells under various conditions. Separations were carried out using carboxylated dextran-coated super-paramagnetic particles as described earlier with variations: separations were carried out either in complete culture medium (RPMI+10% FCS) or in serum free X-Vivo 20 medium (Lonza; contains human serum albumin, HSA), or chemically-defined hybridoma medium (Invitrogen) at 4° C. or 37° C. In this example, dead-cell depletion was achieved under all conditions with highly efficient depletion observed in complete medium and in serum-free, X-Vivo medium; lowest yields of viable cells were obtained using the latter. Data is presented in FIG. 8.

These results demonstrate that dextran-coated particles are effective and versatile in depleting dead cells under a broad range of conditions. Furthermore, they show that the binding and separation milieu can be modified in order to modulate efficiency and yield.

The invention claimed is:

1. A method of improving the viability and/or productivity of a cell in order to generate improved yields of cells or particular products expressed by a cell culture, the method comprising the steps of:
   contacting a cell population of the culture with carboxylated and/or amino dextran under conditions suitable to permit binding between the carboxylated and/or amino dextran and any dead cells or cells undergoing programmed cell death present in the cell culture, wherein the carboxylated and/or amino dextran is packed or provided in a column to which the cell population is added;
   removing at least some of the cell-bound carboxylated and/or amino dextran from said cell culture; and
   culturing the cell culture to provide an improved yield of cells and/or improved product expressed by the cells of the cell culture.

2. A method of improving the viability and/or productivity of a cell in order to generate improved yields of cells or particular products expressed by a cell culture, the method comprising the steps of:
   contacting a cell population of the culture with carboxylated and/or amino dextran under conditions suitable to permit binding between the carboxylated and/or amino dextran and any dead cells or cells undergoing programmed cell death present in the cell culture, wherein the carboxylated and/or amino dextran is adhered, bound, immobilized and/or otherwise associated with a scaffold material to be added to the cell population;
   removing at least some of the cell-bound carboxylated and/or amino dextran from said cell culture; and
   culturing the cell culture to provide an improved yield of cells and/or improved product expressed by the cells of the culture.

3. A method of improving the viability and/or productivity of a cell in order to generate improved yields of cells or particular products expressed by a cell culture, the method comprising the steps of:
- contacting a cell population of the culture with carboxylated and/or amino dextran under conditions suitable to permit binding between the carboxylated and/or amino dextran and any dead cells or cells undergoing programmed cell death present in the cell culture;
- removing at least some of the cell-bound carboxylated and/or amino dextran from said cell culture, wherein at least some of the cell-bound carboxylated and/or amino dextran is removed from the cell population by filtration, density separation, flow cytometry/cell sorting and/or affinity chromatography techniques; and
- culturing the cell culture to provide an improved yield of cells and/or improved product expressed by the cells of the cell culture.

4. A method of improving the viability and/or productivity of a cell in order to generate improved yields of cells or particular products expressed by a cell culture, the method comprising the steps of:
- contacting a cell population of the culture with carboxylated and/or amino dextran under conditions suitable to permit binding between the carboxylated and/or amino dextran and any dead cells or cells undergoing programmed cell death present in the cell culture, wherein the carboxylated and/or amino dextran is provided in the form of a micro- or nanoparticle and the micro- or nanoparticles further comprise a magnetic material;
- removing at least some of the cell-bound carboxylated and/or amino dextran from said cell culture, wherein at least some of the cell-bound carboxylated and/or amino dextran is removed from the cell population via the application of a magnetic field; and
- culturing the cell culture to provide an improved yield of cells and/or improved product expressed by the cells of the cell culture wherein the carboxylated and/or amino dextran is provided in the form of a micro- or nanoparticle, wherein the micro- or nanoparticles further comprise a magnetic material and at least some of the cell-bound carboxylated and/or amino dextran is removed from the cell population via the application of a magnetic field.

* * * * *